United States Patent
Kinbara et al.

(10) Patent No.: US 6,336,049 B1
(45) Date of Patent: Jan. 1, 2002

(54) ELECTRODE STRUCTURE FOR REDUCING IRRITATION TO THE SKIN

(75) Inventors: Matsuro Kinbara; Kohji Maruyama, both of Ibaraki (JP)

(73) Assignee: Nitto Denko Corporation, Osaka (JP)

( * ) Notice: Subject to any disclaimer, the term of this patent is extended or adjusted under 35 U.S.C. 154(b) by 0 days.

(21) Appl. No.: 09/348,756

(22) Filed: Jul. 7, 1999

(30) Foreign Application Priority Data

Jul. 8, 1998 (JP) .................................................. 10-193387
Dec. 16, 1998 (JP) .................................................. 10-357957

(51) Int. Cl.⁷ .................................................. A61N 1/04
(52) U.S. Cl. .............................. 607/148; 600/393; 604/20
(58) Field of Search .............................. 604/20; 607/115, 607/142, 148, 152, 153; 600/374, 393, 395–397; 606/41, 32

(56) References Cited

U.S. PATENT DOCUMENTS

| 4,141,359 A | * | 2/1979 | Jacobsen et al. | ................ | 604/20 |
| 4,919,648 A | * | 4/1990 | Sibalis | ............................. | 604/20 |
| 5,002,527 A | * | 3/1991 | Reller et al. | ..................... | 604/20 |
| 5,147,297 A | * | 9/1992 | Myers et al. | ..................... | 604/20 |
| 5,284,471 A | | 2/1994 | Sage, Jr. | ........................... | 604/20 |
| 5,295,482 A | * | 3/1994 | Clare et al. | ..................... | 607/142 |
| 5,310,403 A | * | 5/1994 | Haynes | ............................. | 604/20 |
| 5,354,321 A | * | 10/1994 | Berger | ............................. | 607/75 |
| 5,380,272 A | * | 1/1995 | Gross | ............................. | 604/20 |
| 6,018,680 A | * | 1/2000 | Flower | ............................. | 604/20 |
| 6,078,842 A | * | 6/2000 | Gross et al. | ................... | 607/152 |

FOREIGN PATENT DOCUMENTS

| EP | 0 461 680 | 12/1991 |
| EP | 0 513 879 | 11/1992 |

\* cited by examiner

*Primary Examiner*—Kennedy Schaetzle
(74) *Attorney, Agent, or Firm*—Wenderoth, Lind & Ponack, L.L.P.

(57) ABSTRACT

An electrode structure containing plural electrode elements each comprising an electrode and an electrolyte layer laminated thereon, the electrode of each electrode element being connected to a power supply and the electrolyte layer to be in contact with the skin, wherein the plural electrode elements are insulated from each other and the electrode of each element is electrically connected to a resistor that limits the current flowing through this electrode, the resistor having a resistance that is ⅕–5 times the resistance of the skin. The present invention provides an electrode structure capable of making the density of the current flowing to the skin constant, irrespective of the electrification method, and capable of reducing irritation due to the electrification.

17 Claims, 7 Drawing Sheets

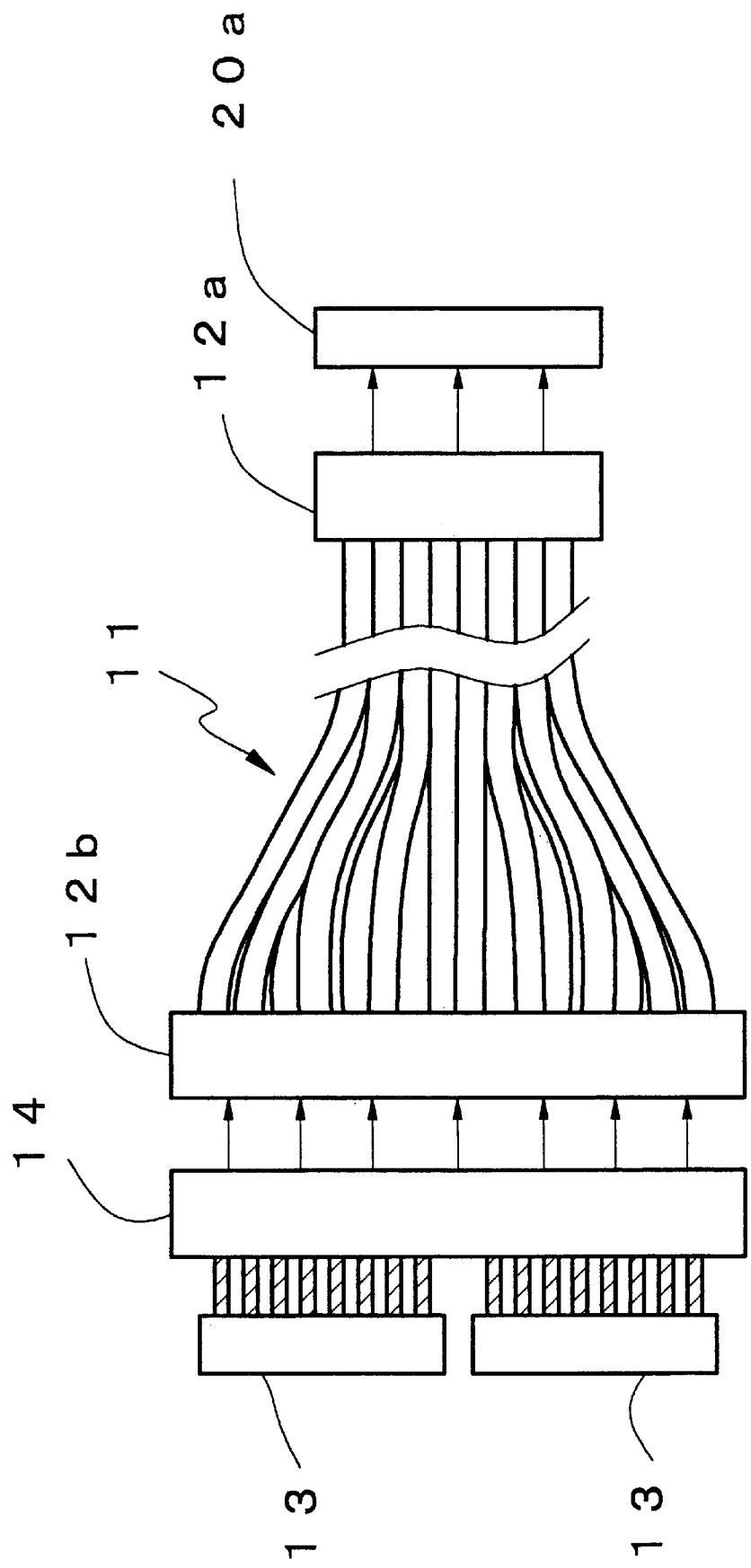

ELECTRODE STRUCTURE FOR REDUCING IRRITATION TO THE SKIN

TECHNICAL FIELD OF THE INVENTION

The present invention relates to an electrode structure. More particularly, the present invention relates to an electrode structure capable of reducing irritation to the skin which is caused by electrification, irrespective of the method of electrification.

BACKGROUND OF THE INVENTION

An electrode structure for the living body, which is used for iontophoresis or high-frequency diathermy knife, generally has a structure wherein an electrode and an electrolyte layer (sometimes containing a drug) are sequentially laminated on an insulating substrate. In most cases, the electrode consists of a single electrode, and an electrolyte layer is laminated on this single electrode.

With this electrode structure, the electrode is connected with a power supply and the electrolyte layer is brought into contact with the skin of a living body. When electrified, however, the current flows concentratedly through the area where electrical resistance of the skin is low, so that the density of the current flowing in the area becomes high. As a result, the high current density in this area irritates the skin, which sometimes damages or burns the skin tissue. When the skin has been damaged from the beginning, the current easily flows concentratedly in such area due to the low resistance of the area, thereby increasing the frequency of burn in this area.

To solve these problems, U.S. Pat. No. 4,416,274 proposes an apparatus capable of retaining the ion to be injected into an electrode to be used for a living body for an ion transfer-limited ionization treatment, which apparatus being formed to prevent ions from moving in the direction generally parallel to the surface of the skin or tissue, and U.S. Pat. No. 4,950,229 and U.S. Pat. No. 5,284,471 propose an apparatus for electrode to be used for iontophoresis, wherein the transmitter including an ionic drug is divided. According to these apparatuses, however, the flow of the current in the transverse direction (direction parallel to the skin surface) within the device that retains the ions to be injected (transmitter including an ionic drug) can be prohibited but that of the current in the transverse direction in a single plate electrode cannot be prohibited. This in turn results in the concentration of the current to the part of the skin of the living body having low resistance, thereby preventing uniform current density.

Moreover, U.S. Pat. No. 5,310,403 proposes a drug delivery apparatus by the introduction of ions, which has a circuit wherein constant current circuit is formed per plural divided electrodes (each divided electrode including an electrode and an apparatus retaining an ionic drug). This apparatus, nevertheless, comprises a constant current circuit formed per each divided electrode, so that it limits the method of electrification, makes the apparatus construction complicated and poses cost problems.

SUMMARY OF THE INVENTION

The present invention aims at solving the above-mentioned problems and provides an electrode structure capable of making the density of the current flowing to the skin constant, irrespective of the electrification method, and capable of reducing irritation due to the electrification.

Such object can be achieved by the present invention. Accordingly, the present invention provides the following.

(1) An electrode structure comprising plural electrode elements each comprising an electrode and an electrolyte layer laminated thereon, the electrode of each electrode element being connected to a power supply and the electrolyte layer to be in contact with the skin, wherein the plural electrode elements are insulated from each other and the electrode of each element is electrically connected to a resistor that limits the current flowing through this electrode, said resistor having a resistance that is $1/5$–5 times the resistance of the skin. (2) The electrode structure of (1) above, wherein the electrode elements are insulated from each other on an insulating substrate by the aid of a partition, and the electrode of each electrode element has a resistive element having a resistance that is $1/5$–5 times the resistance of the skin. (3) The electrode structure of (2) above, wherein each electrode element is disposed on one side of the insulating substrate and insulated from other electrode elements by a partition, and wherein the resistive element having a resistance that is $1/5$–5 times the resistance of the skin is disposed on the other side of the insulating substrate at the position corresponding to a mating electrode element, each electrode of the electrode element and the corresponding resistive element being electrically connected via a conductive path formed in the insulating substrate. (4) The electrode structure of (3) above, wherein the insulating substrate has a wiring layer on the other side of the substrate, the wiring layer being connected to a part of the corresponding resistive element, and having a terminal connecting a wiring for connection to a power supply. (5) The electrode structure of (2) above, wherein each electrode element is disposed on one side of the insulating substrate and insulated from other electrode elements by a partition, the electrode of each electrode element is electrically connected, on the other side of the insulating substrate, to a wiring for connection to a power supply via a conductive path formed in the insulating substrate, and the wiring is connected to a resistive element having a resistance that is $1/5$–5 times the resistance of the skin. (6) The electrode structure of (5) above, wherein the wiring is laid on a tongue part projecting from a part of the insulating substrate in the extending direction of the substrate, each end of the wire being connected to the connector for wire extension fixed on the tip of the tongue part, wherein the connector for wire extension is connected to a connector on one end of an electric cable for wire extension, and an integration type connector equipped with resistive elements having a resistance that is $1/5$–5 times the resistance of the skin is connected to a connector on the other end of the electric cable, thereby electrically connecting the resistive elements to the wiring. (7) The electrode structure of (1), (2), (3) or (5) above, wherein the electrode of each electrode element has a circular or polygonal shape and an area of less than 1 cm$^2$. (8) The electrode structure of (1), (2), (3) or (5) above, wherein the electrode of each electrode element comprises a carbon layer and a silver-containing layer formed on the carbon layer. (9) The electrode structure of (1), (2), (3) or (5) above, wherein the electrode of each electrode element comprises a carbon layer and a silver, silver chloride-containing layer formed on the carbon layer. (10) The electrode structure of (8) or (9) above, wherein the carbon layer comprises a composition comprising fine carbon particles and a binder resin. (11) The electrode structure of (3) above, wherein the resistive element comprises a composition comprising fine carbon particles and a binder resin. (12) The electrode structure of (2), (3) or (5) above, wherein the partition is made from a flexible insulating material. (13) The electrode structure of (2), (3) or (5) above, wherein the partition has a shape permitting adhesion to the side of each electrode element and is a formed article having a thickness of not less than 0.1 mm and a height of 1–5 mm. (14) The electrode structure of (2), (3) or (5) above, wherein the partition and the insulating substrate form an integrated product.

According to the electrode structure of the present invention, plural electrode elements are insulated from each other, so that the current does not flow between the adjacent electrode elements. Moreover, the electrode of each electrode element is electrically connected to a resistive element that limits the current flowing through the electrode, whereby the concentrated flow of the current to an electrode element that comes into contact with the area of the skin having a lower resistance can be prevented. Therefore, the current flows at about the same current density, irrespective of the resistance of the area of the skin with which each electrode element comes into contact. In consequence, the current density becomes constant throughout the whole electrode structure and irritation by electrification and burn can be reduced. By merely connecting each electrode of plural electrode elements to the same power supply for electrification, the current density can be equalized, even when electrification methods are different. Thus, the electrification method is not limited. The construction wherein plural electrode elements are insulated from each other on an insulating substrate by the aid of a partition ensures insulated division of plural electrode elements and integration of plural electrode elements. This enables provision of a highly reliable electrode structure having superior handling property. In addition, when a wiring for connection to a power supply is connected to each electrode of plural electrode elements and a resistive element that limits current is exchangeably connected to the wiring, the resistive element can be exchanged easily. Moreover, when a resistive element that limits the current is set on the insulating substrate, plural resistive elements and plural electrode elements can be integrated, thereby further improving the handling property of the electrode structure.

BRIEF DESCRIPTION OF THE DRAWINGS

FIG. 1(A) and FIG. 1(B) show one embodiment of the electrode structure of the present invention, wherein FIG. 1(A) is a plan view and FIG. 1(B) is a sectional view of FIG. 1(A) along the line X–X'.

FIGS. 5(A), 5(B) and 5(C) show another embodiment of the electrode structure of the present invention, wherein FIG. 5(A) is a plan view of one side of the insulating substrate, FIG. 5(B) is a sectional view of FIG. 5(A) along the line X–X' and FIG. 5(C) is a plan view of the other side of the insulating substrate.

DETAILED DESCRIPTION OF THE INVENTION

The present invention is explained in detail in the following.

The electrode structure of the present invention comprises plural electrode elements each comprising an electrode and an electrolyte layer laminated thereon. The plural electrode elements are insulated from each other. The electrolyte layer of each electrode element is brought into contact with the skin of a living body, and the electrode of each electrode element is connected to a power supply and electrically connected to a resistive element (resistive element having a resistance that is 1/5–5 times the resistance of the skin) that limits the current flowing through the electrode.

Figure 1:
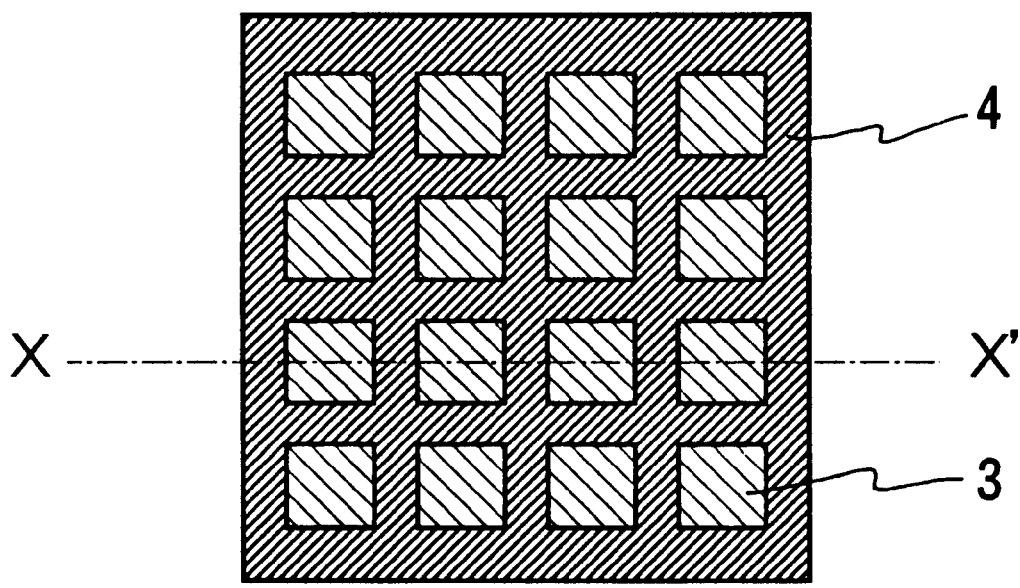
Figure 1:
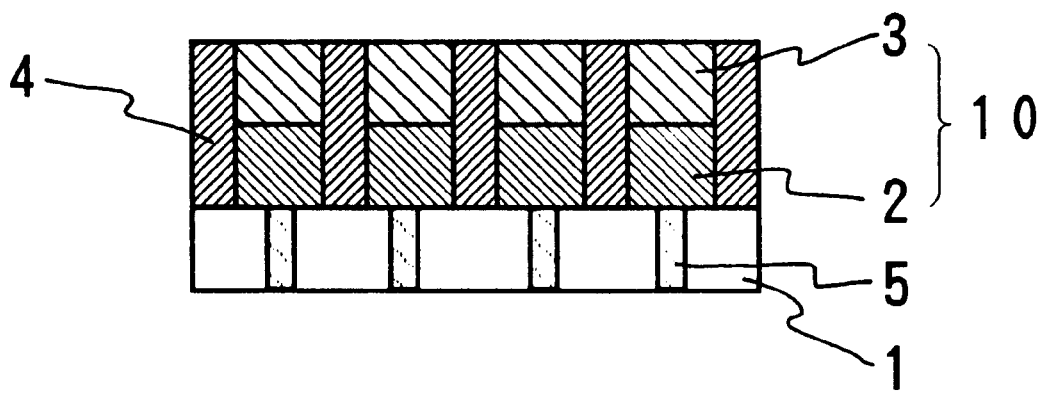
Figure 2:
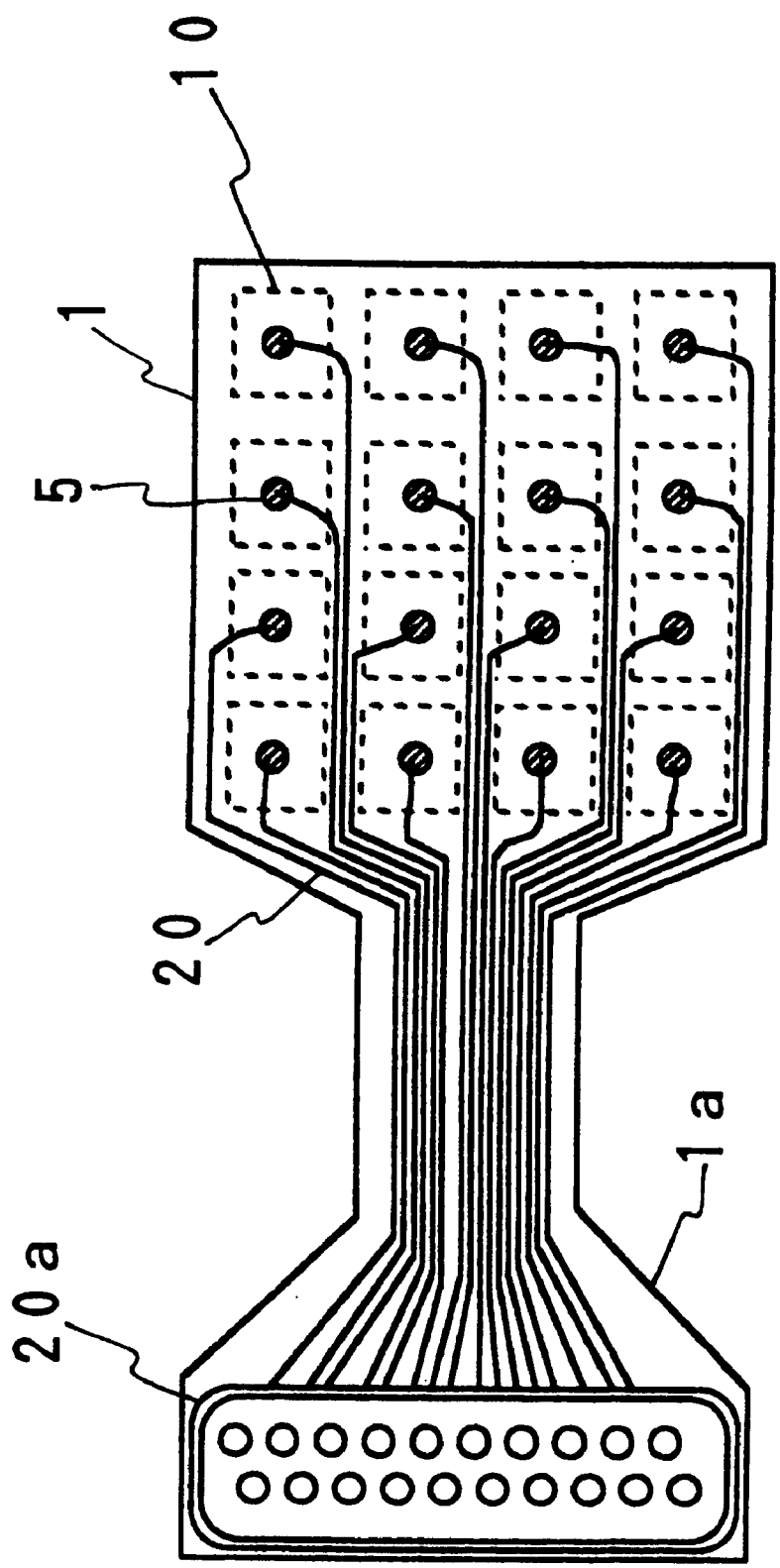
FIG. 2(A) shows the wiring for connection to a power supply in the electrode structure of FIG. 1
FIG. 2(B) shows the connection between the wiring and a resistive element.

FIGS. 1, 2 show one embodiment of the inventive electrode structure. In this electrode structure, sixteen electrode elements 10, each comprising an electrode 2 and an electrolyte layer 3 are disposed in a matrix configuration on one side (surface) of an insulating substrate 1, and adjacent electrode elements are insulated from each other by a partition 4. The insulating substrate 1 has a conductive path 5 corresponding to each electrode element 10, and the electrode 2 of each electrode element 10 is in contact with one end of the conductive path 5.

On the other side (back) of the insulating substrate 1 is exposed the other end of each conductive path 5, with which one end of a wiring 20 for connection to a power supply is connected. Thus, the electrode 2 of each electrode element 10 is electrically connected to the power supply.

The wiring 20 for connection to a power supply is laid on a tongue part 1a projecting from a part of the insulating substrate 1 in the extending direction of the substrate, each end of the wire connecting to a connector 20a for wire extension, which is fixed on the tip of the tongue part 1a in the direction of the projection. The connector 20a has a configuration where two rows of terminals are disposed such that they are staggered in position, which configuration being called a half pitch connector to miniaturize the structure.

As shown in FIG. 2(B), the above-mentioned connector 20a is connected to a connector 12a on one end of an electric cable 11 for wire extension, and a resistive element integration type connector 14 is connected to a connector 12b on the other end of the electric cable. The resistive element integration type connector 14 consists of two collective resistors 13 each comprising eight resistive elements having a resistance that is 1/5–5 times the resistance of the skin, whereby each resistive element is connected to one of the wirings 20 for connection to a power supply. The connector 12a on one end of the electric cable 11 for wire extension is a half pitch connector corresponding to the connector 20a formed on the tongue part 1a of the insulating substrate 1.

Figure 3:
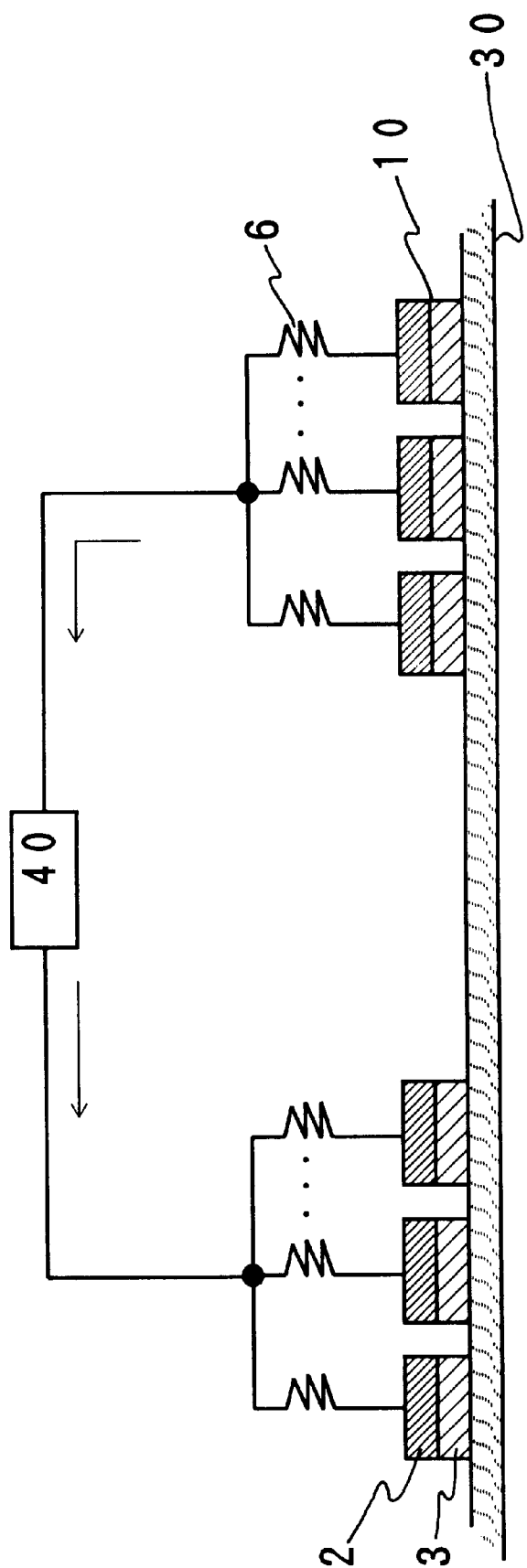
FIG. 3 is a schematic view showing the electrode structure of the present invention during use.

FIG. 3 shows the electrode structure of the present invention during use. As shown in this Figure, the electrode structure of the present invention is used by bringing the surface of the electrolyte layer 3 of each electrode element 10 into contact with the skin 30, followed by electrification. As the power supply 40, various power supplies can be used depending on the purpose. For example, a direct constant current power supply, pulse current power supply, high frequency power supply and the like can be used.

Each electrode element 10 is insulated from other electrode elements by the partition 4, so that the electrifying current does not flow between adjacent electrode elements (between electrode and electrode, between electrode and electrolyte layer, or between electrolyte layer and electrolyte layer). Inasmuch as the electrode 2 of each electrode element 10 is electrically connected to a resistor 6 having a resistance that is 1/5–5 times the resistance of the skin, for example, the electrode element set on a wounded skin has lower contact resistance between the electrode element and the skin. Despite the tendency of the current to flow concentratedly through this electrode 2 of the electrode element 10, the flow is limited by the resistor 6 having a resistance that is 1/5–5 times the resistance of the skin, and the concentrated flow of the current is prevented.

The resistor 6 to be connected to the electrode 2 of the electrode element 10 is set to have a resistance that is 1/5–5 times the resistance of the skin, because the value smaller than 1/5 time the resistance of the skin shows insufficient effect of preventing concentration of the current and allows the current density to grow too high at a local site, thus creating a high risk of causing a burn, whereas when it is greater than 5 times, an excessive voltage is needed to obtain the current necessary for iontophoresis, diathermy knife and the like. The resistance of the human skin is about 5–100 $k\Omega/cm^2$ at a frequency of not greater than 100 Hz, which decreases with increasing frequencies, and becomes about several hundred $\Omega/cm^2$ at a frequency of not less than 100 kHz (see T. Yamamoto, Y. Yamamoto, "Electrical properties of the epidermal stratum corneum" Medical and Biological Engineering, March 1976, p. 151).

The material to be used for insulating substrate 1 is free of limitation and any material can be used as long as it has an insulating property. Specific examples include polyimide, polyethylene terephthalate, polypropylene, polyamide and the like. From the aspects of heat resistance, moisture resistance and dimensional stability, polyimide and polyethylene terephthalate are preferably used. The shape of the insulating substrate 1 is typically a sheet or a film.

The size and shape of the upper surface of the electrode element 10 (the surface of electrolyte layer 3 that comes into contact with the skin) are not particularly limited and can be determined as appropriate depending on the living body to be the target, object, number of electrode elements and the like. It is generally preferable that the total area of the upper surface of the electrode elements 10 be 2–400 $cm^2$, preferably 4–200 $cm^2$.

In the embodiment of FIG. 1, sixteen electrode elements 10 have been disposed. The number of the electrode elements 10 is preferably not less than 10, wherein more number thereof results in a highly constant current density.

The material of the electrode 2 is subject to no particular limitation as long as it is conductive, and is exemplified by a film of conductive coating, metal foil and the like.

The conductive coating is exemplified by silver coating (e.g., DOTITE FA-353 manufactured by FUJIKURA KASEI CO., LTD.), carbon coating (e.g., carbon conductive coating MRX-713J manufactured by TAMURA CORPORATION) and the like. The metal foil is exemplified by foils of aluminum, copper, silver and the like. In the case of a conductive coating film, it may be formed directly on the insulating substrate, but a coating film may be also formed on a resin film, such as polyethylene terephthalate film and the like, and then a resin film having this coating film may be adhered solidly to the surface of an insulating substrate.

Figure 4:
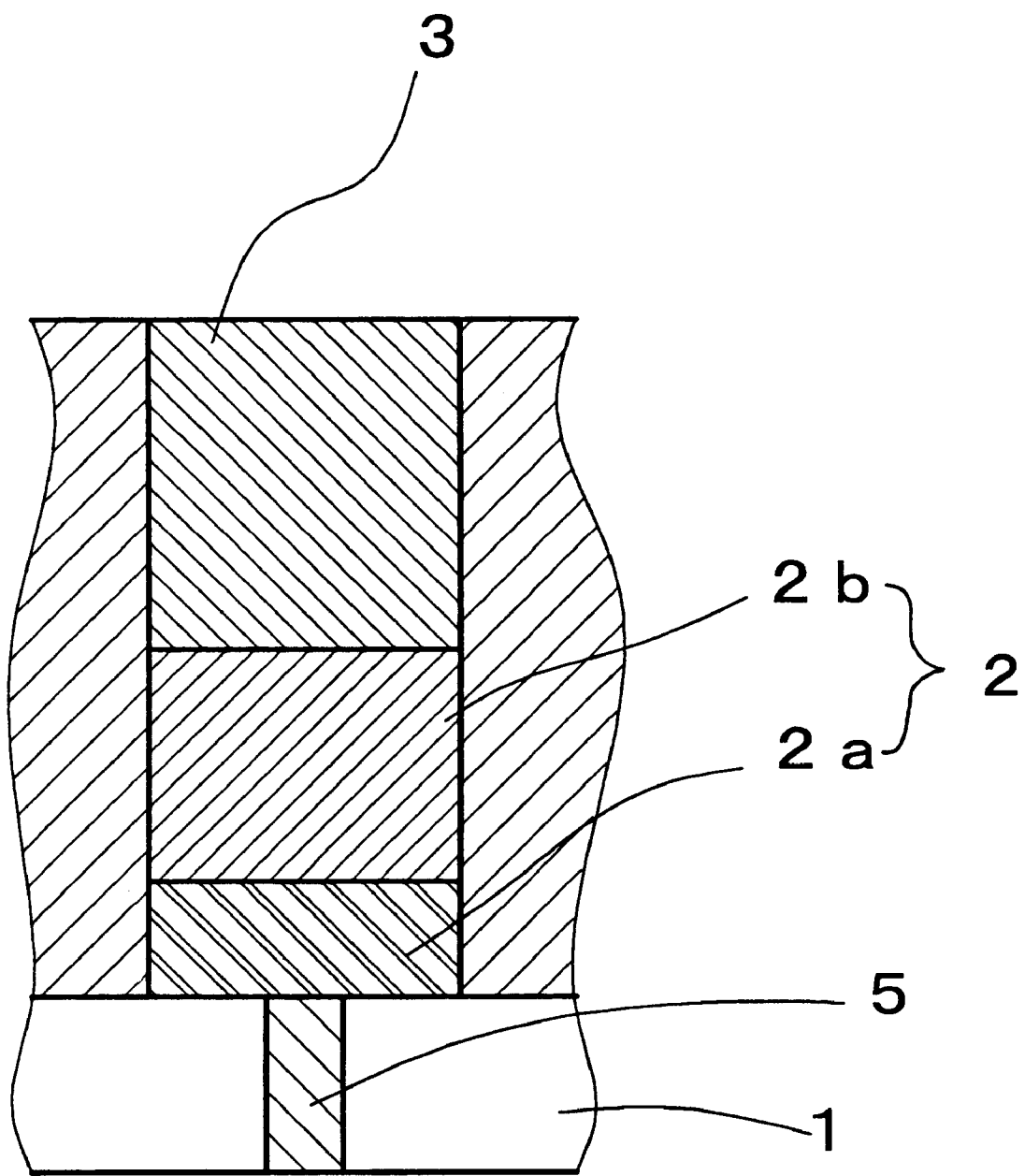
FIG. 4 shows a preferable structure of the electrode constituting the electrode element of the inventive electrode structure.

While the electrode 2 is a single layer in the embodiment of FIG. 1, a laminate consisting of the lower layer 2a and the upper layer 2b may be used, as shown in FIG. 4. By making the electrode a laminate, the electrode has an improved electrification property, and the electrode can be easily modified to give a construction that fits better for the electrode structure for a positive electrode or a negative electrode.

The lower layer 2a is preferably made from a material free of electrochemical changes. Such material is preferably a carbon. This carbon is preferably a coating film made from a composition (coating) containing fine carbon particles and a binder resin. The binder resin used here is exemplified by phenolic resin, polyester resin, epoxy resin, acrylic resin and the like. Such coating is exemplified by DOTITE FC-415 manufactured by FUJIKURA KASEI CO., LTD., carbon conductive coating MRX-713J manufactured by TAMURA CORPORATION and the like. The lower layer 2a comprising a carbon layer can be formed by, for example, screen printing.

The upper layer 2b preferably contains a metal material having superior conductivity, such as silver. Examples of such layer include a silver-plated layer, a silver, silver chloride layer obtained by electrolysis of a silver-plated layer in brine, a coating film layer made from a coating containing fine silver powder and a binder resin, and a coating film layer made from a coating containing fine silver powder, fine silver chloride powder and a binder resin. As the binder resin, phenolic resin, polyester resin, epoxy resin, acrylic resin and the like can be used.

When an electrode structure is used as a positive electrode, the upper layer 2b is preferably a silver-containing layer, which is exemplified by silver-plated layer and a coating film layer comprising a silver powder and a binder resin. When the electrode structure is used as a negative electrode, the upper layer 2b is preferably a silver, silver chloride-containing layer, which is exemplified by a coating film layer comprising a silver powder, a silver chloride powder and a binder resin, and a silver, silver chloride layer obtained by electrolysis of a silver-plated layer in brine.

As the silver coating, DOTITE FA-353 manufactured by FUJIKURA KASEI CO., LTD. can be used and as the silver, silver chloride coating, DOTITE XA-450 manufactured by FUJIKURA KASEI CO., LTD. can be used. These coatings are screen printed to give the upper layer 2b made from a silver-containing layer or a silver, silver chloride-containing layer. The silver-containing layer and the silver, silver chloride-containing layer may be used as they are or after application of silver plating when the surface is desired to be 100% silver.

The thickness of the upper layer made from a silver-containing layer or a silver, silver chloride-containing layer is subject to no particular limitation, but the amount to be attached needs to be more than the conversion amount of Ag→AgCl or AgCl→Ag, which is calculated from the electrification charge of iontophoresis.

The surface shape of the electrode 2 is subject to no particular limitation, but it is preferably a circle or polygon, wherein the area preferably does not exceed 1 $cm^2$ for the prevention of concentration of the current. The electrode 2 is smaller than conventional single electrodes; hence it is preferably made into a 1–10 mm square in view of processability and handling property. When one side is smaller than 1 mm, processing becomes difficult, whereas when one side is greater than 10 mm, the density of the current electrified on the skin cannot be equalized easily. The thickness of the electrode 2 is subject to no particular limitation, but it is generally about 10–100 $\mu m$, preferably about 20–50 $\mu m$.

The electrolyte layer 3 to be laminated on the electrode 2 consists of an electrolyte solution and a material capable of retaining this solution. Examples of the electrolyte solution include physiological saline or aqueous solution containing a drug capable of ionic dissociation. The material capable of retaining the electrolyte solution is subject to no particular limitation as long as it can retain the solution and may be, for example, absorbent cotton, sponge, gelling material and the like, with preference given to a gelling material that retains the electrolyte solution.

Examples of the gelling material include natural polysaccharides such as starch, karaya rubber, tragacanth rubber, xanthan gum and the like; vinyl resin such as poly(vinyl alcohol) obtained by partial saponification, poly(vinyl formal), poly(vinyl methyl ether) and copolymers thereof, poly(vinylpyrrolidone), poly(vinyl methacrylate) and the like; acrylic resin such as partially saponified polyacrylic ester, poly(acrylic acid-acrylamide) and the like; and the like. These natural polysaccharides and synthetic resins having hydrophilicity are softened with water and/or alcohol such as polyethylene glycol, glycerol and the like to give a flexible sheet gel having self-shape retention property and skin contactability. The thickness of the electrolyte layer 3 is generally about 0.2–10 mm, preferably about 1–5 mm.

When the electrode structure of the present invention is used for iontophoresis, the drug-containing aqueous solution is contained in an electrolyte layer 3 of the electrode structure for a positive electrode or a negative electrode, according to the ionic state of the drug in the aqueous solution. For example, when the drug is present as cations in the aqueous solution, it is used as an electrolyte solution contained in the electrolyte layer of the electrode structure for a positive electrode. When the drug is present as anions in the aqueous solution, it is used as an electrolyte solution contained in the electrolyte layer of the electrode structure for a negative electrode. In both cases, the electrolyte solution to be contained in the electrolyte layer of the other electrode structure is physiological saline.

The partition 4 is subject to no particular limitation as long as it is made from a composition containing an insulating material. In view of the fact that the inventive electrode structure is adhered to the skin, it is preferably made from a composition containing an insulating material having flexibility.

The flexible insulating material may be, for example, soft silicone resin, styrene thermoplastic elastomer, olefin thermoplastic elastomer, propylene copolymerized soft resin and the like, with preference given to styrene thermoplastic elastomer having suitable flexibility. Examples of the styrene thermoplastic elastomer include RABALON SJ-4400 manufactured by Mitsubishi Chemical Corporation. It is also possible to use the same material as the insulating substrate 1.

While the method for forming the partition 4 and the shape thereof are subject to no particular limitation, it preferably has a shape allowing coherence to the side shape of each electrode element 10. As shown in FIG. 1(A), for example, when the electrode element 10 is rectangular and the elements are aligned vertically and transversely, the partition 4 preferably has a shape of a curb that allows coherence to the side shape of each electrode element 10. The partition 4 formed into a desired shape is set on the insulating substrate 1 between electrode elements 10 using an adhesive.

The partition 4 may be integrally formed with the insulating substrate 1. In this case, the part corresponding to the thickness of the electrode 2 and electrolyte layer 3 may be cut off from a thick insulating substrate 1, or an integrated article of insulating substrate 1 and partition 4 may be formed using a mold.

The height of the partition 4 may be any as long as the electrolyte layer 3 does not overreach the partition, so that transverse diffusion of the current will not occur, which is preferably about 1–5 mm. The thickness of the partition is preferably not less than 0.1 mm.

Figure 5:
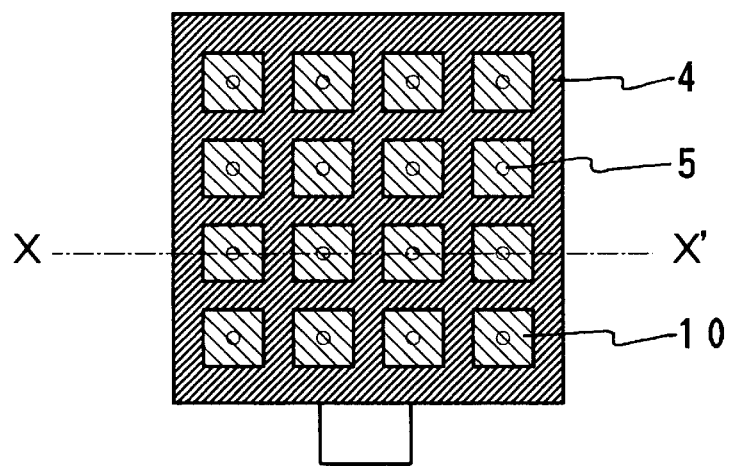
Figure 5:
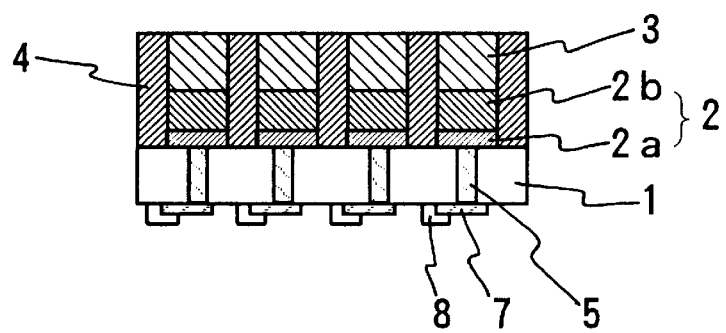
Figure 5:
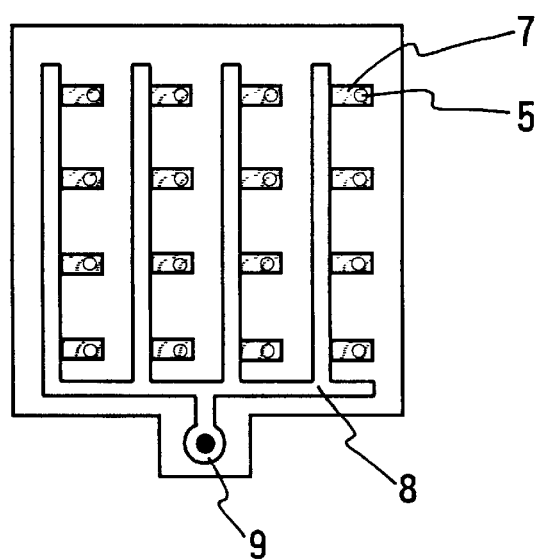

FIG. 5 shows another embodiment of the electrode structure of the present invention. This electrode structure comprises a resistive element 7 wherein a resistor having a resistance that is 1/5–5 times the resistance of the skin, which is to be electrically connected to the electrode 2 of each electrode element 10, is set on the other side (back) of the insulating substrate 1, and a wiring layer 8 that connects each resistive element 7 is set on the other side of the insulating substrate 1, the wiring for connection to a power supply being connected to a terminal 9 formed on this wiring layer 8.

Each resistive element 7 is set on the other side (back) of the insulating substrate 1 at the position corresponding to each electrode element 2, wherein the mating electrode element 2 and resistive element 7 are electrically connected via a conductive path 5. The wiring layer 8 forms a shape like teeth of a comb, allowing superposing part of each resistive element 7, and has a terminal 9 on one end thereof.

The resistive element 7 may be a commercial chip resistor. For lower production cost, however, a paste containing fine carbon particles and a binder resin may be formed into a shape affording a certain resistance by, for example, screen printing. The usable binder resin is exemplified by phenolic resin, polyester resin, epoxy resin, acrylic resin and the like. The paste is exemplified by DOTITE XC-155U manufactured by FUJIKURA KASEI CO., LTD. The wiring layer 8 is formed by screen printing a conductive paste, such as a low resistant silver paste. Examples of the paste include DOTITE FA-353 manufactured by FUJIKURA KASEI CO., LTD.

According to the electrode structure of the present invention, the conductive path 5 to be formed on the insulating substrate 1 is prepared by forming a fine through hole in the insulating substrate 1, and filling a conductive material therein. In this case, for example, a method comprising printing a carbon-containing coating on the insulating substrate 1 having a through hole at a predetermined position to form a carbon layer to be the electrode 2 (lower layer 2a of the electrode) and concurrently packing a conductive material in the through hole, or a method comprising printing the back of the insulating substrate 1 having a through hole at a predetermined position, with a carbon resistant paste for forming a resistive element to form a resistive element 7 and concurrently packing a conductive material in the through hole, may be employed. The resistive element 7 and electrode element 10 can be electrically connected with ease by these methods.

The present invention is explained in detail by illustrative reference examples and examples, to which the present invention is not limited in any way.

Examples 1–5, Comparative Examples 1–4

Eelectrode used

The electrode structure as shown in FIGS. 1, 2 was used. The electrode used was a 17 $\mu$m thick, square (2.5 mm one side) copper foil plated with silver (5 $\mu$m), which was laminated on a polyimide film. The wiring was made of copper with an insulating coating applied thereon.

A curb-like partition (width 1.5 mm, height 2 mm) was made from a styrene thermoplastic elastomer (RABALON SJ-4400 manufactured by Mitsubishi Chemical Corporation) to separate the above-mentioned electrode elements at the distance of 1.5 mm and laminated on the polyimide film.

As the electrolyte layer, a conductive gel was used, which was prepared by impregnating, by 90 wt %, oblate (Drug Oblaat manufactured by NIIGATA OBLAAT CO., LTD.) with physiological saline (NaCl 0.9 wt %).

Resistive Element for Limiting Current

A collective element consisting of 1 k$\Omega$, 10 k$\Omega$, 22 k$\Omega$, 50 k$\Omega$ and 100 k$\Omega$ resistors was used, wherein each resistive element could be exchanged with a connector.

Power Supply

As the direct constant current source, a portable constant current source circuit was used, which was newly prepared utilizing the constant current property of a transistor. For a pulse and high frequency power supply, a multifunction synthesizer type 1930 manufactured by NF CORPORATION was used.

Measurement of Current of Electrode Element

The voltage of the resistive element of the positive electrode and the negative electrode was measured by the NR-110 type data collection system manufactured by KEYENCE CORPORATION. The data were collected at 50-second intervals and the measurement data at 5 minutes after electrification were converted into current.

Example 1

To the left forearm of an adult male (measured resistance of the direct current area was about 7 k$\Omega$/cm$^2$) were applied electrode structures (containing 16 positive electrode elements and 16 negative electrode elements, each electrode 2.5 mm□), wherein the positive and negative electrode structures were set at a distance of 20 mm, and the structures were electrified. The resistive element for limiting the current had a resistance of 100 k$\Omega$(converted into area unit resistance of 6.25 k$\Omega$/cm$^2$) and the density of the current flowing through each electrode element in the positive-negative electrode structure was calculated from the voltage applied to the both ends of the resistive element.

Example 2

In the same manner as in Example 1 except that the resistive element connected to each electrode element had a resistance of 50 k$\Omega$(converted into area unit resistance of 3.125 k$\Omega$/cm$^2$), the density was calculated.

Example 3

In the same manner as in Example 1 except that the resistive element connected to each electrode element had a resistance of 22 k$\Omega$(converted into area unit resistance of 1.375 k$\Omega$/cm$^2$), the density was calculated.

Comparative Example 1

In the same manner as in Example 1 except that the resistive element connected to each electrode element had a resistance of 10 k$\Omega$(converted into area unit resistance of 625 $\Omega$/cm$^2$), the density was calculated.

Comparative Example 2

In the same manner as in Example 1 except that the resistive element connected to each electrode element had a resistance of 1 k$\Omega$(converted into area unit resistance of 62.5 $\Omega$/cm$^2$), the density was calculated.

The maximum value, the minimum value and the average value of the current density per each electrode element of the positive electrode structures as obtained in Examples 1–3 and Comparative Examples 1, 2 are shown in Table 1.

TABLE 1

Unit: mA/electrode element

| Electrode No. | Ex. 1 | Ex. 2 | Ex. 3 | Com. Ex. 1 | Com. Ex. 2 |
|---|---|---|---|---|---|
| Electrode 1 | 0.064 | 0.065 | 0.065 | 0.063 | 0.062 |
| Electrode 2 | 0.064 | 0.065 | 0.065 | 0.065 | 0.047 |
| Electrode 3 | 0.065 | 0.065 | 0.070 | 0.064 | 0.058 |
| Electrode 4 | 0.064 | 0.067 | 0.067 | 0.071 | 0.081 |
| Electrode 5 | 0.065 | 0.066 | 0.070 | 0.065 | 0.068 |
| Electrode 6 | 0.064 | 0.068 | 0.067 | 0.068 | 0.065 |
| Electrode 7 | 0.066 | 0.066 | 0.072 | 0.065 | 0.058 |
| Electrode 8 | 0.065 | 0.068 | 0.070 | 0.075 | 0.084 |
| Electrode 9 | 0.065 | 0.067 | 0.069 | 0.072 | 0.084 |
| Electrode 10 | 0.065 | 0.068 | 0.070 | 0.067 | 0.060 |
| Electrode 11 | 0.065 | 0.067 | 0.073 | 0.070 | 0.069 |
| Electrode 12 | 0.066 | 0.069 | 0.067 | 0.092 | 0.106 |
| Electrode 13 | 0.065 | 0.066 | 0.064 | 0.065 | 0.059 |
| Electrode 14 | 0.065 | 0.066 | 0.069 | 0.060 | 0.040 |
| Electrode 15 | 0.065 | 0.067 | 0.067 | 0.070 | 0.080 |
| Ave. current | 0.065 | 0.067 | 0.068 | 0.069 | 0.068 |
| Max. current | 0.066 | 0.069 | 0.073 | 0.092 | 0.106 |
| Min. current | 0.064 | 0.065 | 0.064 | 0.060 | 0.040 |

As shown in Table 1, with the resistor (1 k$\Omega$) for limiting the current, the maximum value of the current density was 2.5 times the minimum value, whereas when the resistance for limiting the current was 22 k$\Omega$, the current density showed dispersion of within about mean±10%, with still less dispersion when the resistance for limiting the current was set to 50 k$\Omega$ and 100 k$\Omega$.

Example 4

The skin (measured resistance in the direct current area about 5 k$\Omega$/cm$^2$) of a 5 month-old female Yucatan miniature swine purchased from CHARLES RIVER JAPAN INC. was cut in 5 cm ×10 cm, and physiological saline was placed on the skin enclosed in a 1% agar gel. In the same manner as in Example 1 with regard to the size, number and position of each electrode element, resistance of resistive element and the like, the current density was measured.

Comparative Example 3

In the same manner as in Example 4 except that the resistive element connected to each electrode element had a resistance of 1 k$\Omega$(converted into area unit resistance of 62.5 $\Omega$/cm$^2$), the current density was measured.

The maximum value, the minimum value and the average value of the current density per each electrode element of the positive electrode structures as obtained in Example 4 and Comparative Example 3 are shown in Table 2.

TABLE 2

Unit: mA/electrode element

| Electrode No. | Ex. 4 | Comp. Ex. 3 |
|---|---|---|
| Electrode 1 | 0.036 | 0.053 |
| Electrode 2 | 0.034 | 0.044 |
| Electrode 3 | 0.035 | 0.047 |
| Electrode 4 | 0.033 | 0.050 |
| Electrode 5 | 0.033 | 0.030 |
| Electrode 6 | 0.033 | 0.044 |
| Electrode 7 | 0.034 | 0.042 |
| Electrode 8 | 0.034 | 0.056 |
| Electrode 9 | 0.032 | 0.027 |
| Electrode 10 | 0.032 | 0.051 |
| Electrode 11 | 0.034 | 0.052 |
| Electrode 12 | 0.031 | 0.032 |
| Electrode 13 | 0.035 | 0.034 |
| Electrode 14 | 0.033 | 0.044 |
| Electrode 15 | 0.035 | 0.058 |
| Ave. current | 0.034 | 0.041 |
| Max. current | 0.036 | 0.058 |
| Min. current | 0.031 | 0.027 |

As shown in Table 2, with the resistor (1 kΩ) for limiting the current as shown in Comparative Example 3, the maximum value of the current density was about 2 times the minimum value, whereas when the resistance for limiting the current was 100 kΩ as in Example 4, the current density showed dispersion of within about mean±10%.

Example 5

In the same manner as in Example 4, except that the skin of the 5 month-old female Yucatan miniature swine purchased from CHARLES RIVER JAPAN INC. was punctured with an about 0.8 mmφ needle to make a hole, the current density was measured.

Comparative Example 4

In the same manner as in Example 5 except that the resistive element connected to each electrode element had a resistance of 1 kΩ (converted into area unit resistance of 62.5 Ω/cm²), the current density was measured.

The maximum value, the minimum value and the average value of the current density per each electrode element of the positive electrodes as obtained in Example 5 and Comparative Example 4 are shown in Table 3.

TABLE 3

Unit: mA/electrode element

| Electrode No. | Ex. 5 | Comp. Ex. 4 |
|---|---|---|
| Electrode 1 | 0.035 | 0.061 |
| Electrode 2 | 0.033 | 0.046 |
| Electrode 3 | 0.034 | 0.051 |
| Electrode 4 | 0.033 | 0.041 |
| Electrode 5 | 0.033 | 0.038 |
| Electrode 6 | 0.032 | 0.034 |
| Electrode 7 | 0.033 | 0.040 |
| Electrode 8 | 0.033 | 0.038 |
| Electrode 9 | 0.032 | 0.039 |
| Electrode 10 | 0.032 | 0.030 |
| Electrode 11 | 0.034 | 0.044 |
| Electrode 12 | 0.033 | 0.043 |
| Electrode 13 | 0.034 | 0.051 |
| Electrode 14 | 0.031 | 0.029 |
| Electrode 15 | 0.034 | 0.062 |
| Ave. current | 0.033 | 0.043 |
| Max. current | 0.035 | 0.062 |
| Min. current | 0.031 | 0.029 |

As shown in Table 3, in the case of a damaged skin with the resistor for limiting the current of 1 kΩ as shown in Comparative Example 4, the maximum value of the current density was about 2 times the minimum value, whereas when the resistance for limiting the current was 100 kΩ as in Example 5, the current density showed dispersion of within about mean±10%. Thus, as in the case of the skin without a wound, decrease in the resistance could be suppressed even in the case of the damaged skin.

Examples 6 and 7, Comparative Examples 5 and 6

Example 6

Two electrode structures shown in FIG. 5 for the positive electrode side and the negative electrode side were prepared as in the following.

A 0.3 mmφ through hole was formed in a 50 μm polyester film substrate at the predetermined position where a carbon layer (lower layer 2a of electrode 2) was to be formed, and carbon conductive coating (FC-415 manufactured by FUJIKURA KASEI CO., LTD.) was screen printed in a thickness of 10 μm, whereby 16 carbon layers (each size 3.5 mm□, each interval 1.5 mm) were formed.

On the back of the film, a carbon resistant paste (XC-155U manufactured by FUJIKURA KASEI CO., LTD.) was screen printed to form a resistive element 7 having a resistance of about 50 kΩ (12.5 kΩ/cm² was the designed value in this example) at the position corresponding to the position where the carbon layer was to be formed. Concurrently, the through hole was filled with the paste to give a conductive path 5, via which the carbon layer and the resistive element were electrically connected. Then, a wiring to connect these resistive elements was formed by screen printing of a silver paste (FA-353, manufactured by FUJIKURA KASEI CO., LTD.).

Then, on the above-mentioned carbon layer, a 30 μm thick silver paste (FA-353, manufactured by FUJIKURA KASEI CO., LTD.) was screen printed to give a silver-containing layer (upper layer 2b of electrode 2) for the positive electrode, and a silver, silver chloride paste (XA-450, manufactured by FUJIKURA KASEI CO., LTD.) was screen printed to give a silver, silver chloride-containing layer for the negative electrode, whereby an electrode 2 was formed.

A curb-like electrode partition (width 1 mm, height 2 mm, pitch 5 mm) that adhered to the side shape of the electrode was formed from a styrene thermoplastic elastomer (RABALON SJ-4400 manufactured by Mitsubishi Chemical Corporation). This partition 4 was fit in between the electrodes on the above-mentioned insulating substrate and adhered to the insulating substrate with an epoxy resin.

As the electrolyte layer 3 for the positive electrode, a gel prepared by impregnating, by 90 wt %, oblate (Drug Oblaat manufactured by NIIGATA OBLAAT CO., LTD.) with 10 wt % aqueous lidocaine hydrochloride solution was used, and as the electrolyte layer 3 for the negative electrode, a gel prepared by impregnating, by 90 wt %, oblate (Drug Oblaat manufactured by NIIGATA OBLAAT CO., LTD.) with 0.9 wt % physiological saline was used to respectively form layers on the silver-containing layer and the silver, silver chloride-containing layer.

As shown in FIG. 3, the obtained electrode structures on the positive electrode side and the negative electrode side were adhered to the left forearm of an adult male (skin resistance about 15 kΩ/cm$^2$) at about 20 mm interval, and electrified with direct constant current (2 mA) for 10 minutes.

Comparative Example 5

Figure 6:
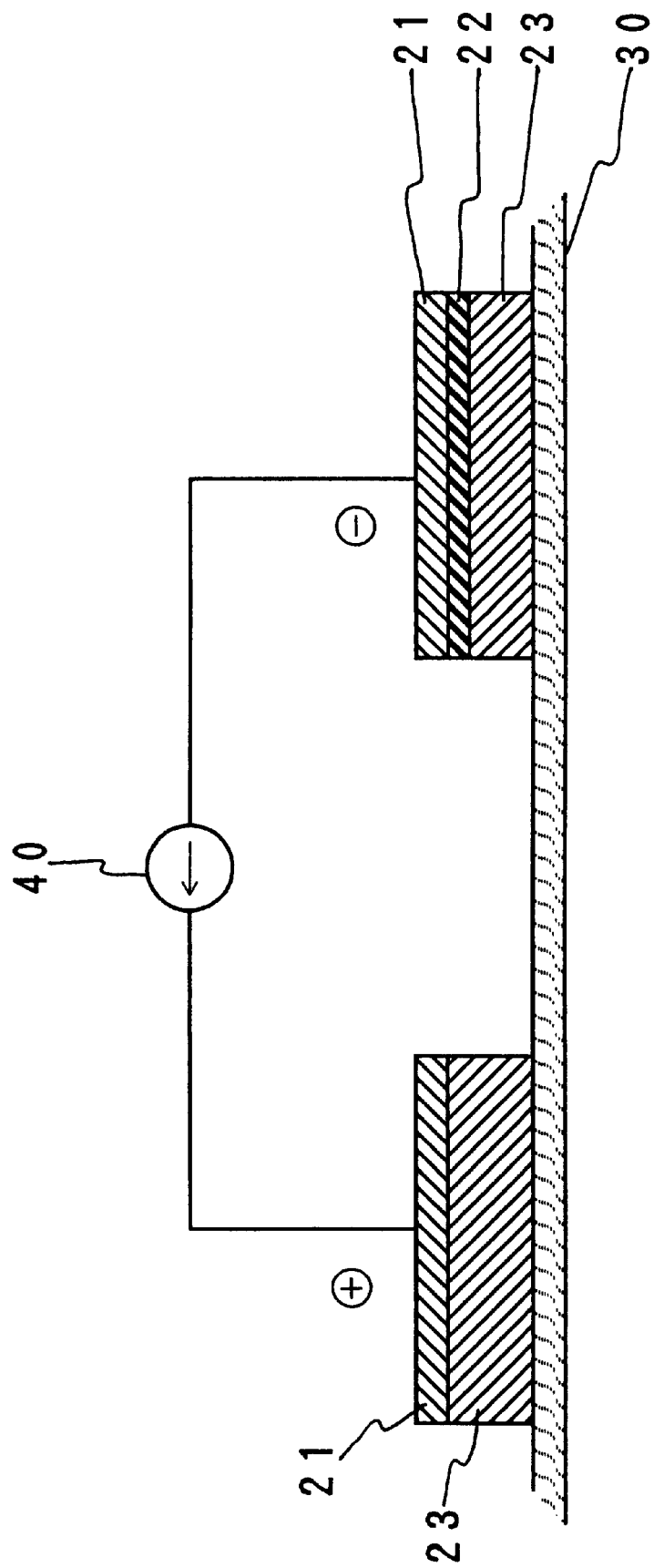
FIG. 6 is a schematic view showing a conventional electrode structure during use.

The electrode structure as shown in FIG. 6 was prepared as in the following.

The single electrode 21 was a silver foil electrode (20 mm□, thickness 30 μm), and a silver chloride layer 22 having a thickness of about 5 μm was formed on the single electrode 21 on the negative electrode side.

An electrolyte layer 23 on the positive electrode side was formed by impregnating about 2 mm thick absorbent cotton with a 10 wt % aqueous lidocaine hydrochloride solution, and an electrolyte layer 23 on the negative electrode side was formed by impregnating about 2 mm thick absorbent cotton with 0.9 wt % physiological saline.

The obtained electrode structures on the positive electrode side and the negative electrode side were adhered to the left forearm of an adult male (skin resistance about 15 kΩ/cm$^2$) at about 20 mm interval as shown in FIG. 3, and electrified with direct constant current (2 mA) for 10 minutes.

As a result of the electrification, the positive electrode side showed a sufficient local anesthesia effect of lidocaine in both Example 6 and Comparative Example 5. Blister due to the concentration of the current was not found in Example 6, but in Comparative Example 5, both the positive electrode side and the negative electrode side showed about 2 mmφ blister due to the local current concentration.

Example 7

The electrode structure for positive electrode and the electrode structure for negative electrode obtained in Example 6 were adhered to the left forearm of an adult male (skin resistance about 15 kΩ/cm$^2$) at about 20 mm interval as shown in FIG. 3, and electrified with direct constant current (1.6 mA) for 5 minutes. As the direct constant current source, a portable constant current source circuit was used, which was newly prepared utilizing the constant current property of a transistor. The current density was determined from the voltage applied to the resistive element 7 of each electrode element. The measurement data at 5 minutes after electrification were converted into current.

Comparative Example 6

In the same manner as in Example 7 except that the coating thickness of the carbon resistant paste was changed to make the resistance of the resistive element about 10 kΩ(2.5 kΩ/cm$^2$), electrode structures for the positive electrode and negative electrode were prepared, and the current density was measured.

The maximum value, the minimum value and the average value of the current density per each electrode element of the positive electrode structures as obtained in Example 7 and Comparative Example 6 are shown in Table 4.

TABLE 4

Unit: mA/electrode element

| Electrode No. | Ex. 7 | Comp. Ex. 6 |
|---|---|---|
| Electrode 1 | 0.105 | 0.104 |
| Electrode 2 | 0.105 | 0.072 |
| Electrode 3 | 0.11 | 0.068 |
| Electrode 4 | 0.109 | 0.083 |
| Electrode 5 | 0.102 | 0.108 |
| Electrode 6 | 0.101 | 0.118 |
| Electrode 7 | 0.11 | 0.071 |
| Electrode 8 | 0.107 | 0.049 |
| Electrode 9 | 0.109 | 0.092 |
| Electrode 10 | 0.111 | 0.081 |
| Electrode 11 | 0.111 | 0.139 |
| Electrode 12 | 0.099 | 0.357 |
| Electrode 13 | 0.114 | 0.071 |
| Electrode 14 | 0.106 | 0.097 |
| Electrode 15 | 0.107 | 0.073 |
| Ave. current | 0.107 | 0.106 |
| Max. current | 0.114 | 0.357 |
| Min. current | 0.099 | 0.049 |

As shown in Table 4, the current density showed dispersion of within about mean±10% in Example 7. However, in Comparative Example 6, the current density was not constant due to the low resistance.

This application is based on patent application Nos. 193387/1998 and 357957/1998 filed in Japan, the contents of which are hereby incorporated by reference.

What is claimed is:

1. An electrode structure comprising:
   a plurality of electrode elements, each of said electrode elements comprising an electrode for connection to a power supply and an electrolyte layer for contact with skin having a resistance, said electrolyte layer being laminated on said electrode;
   an insulating substrate, having a first side and a second side, wherein said electrode elements are disposed on said first side of said insulating substrate, and wherein said electrode elements are insulated from each other by a partition; and
   at least one resistor comprising at least one resistive element having a resistance that is ⅕ to 5 times the resistance of the skin;
   wherein said electrode of each electrode element is electrically connected to said at least one resistive element via a conductive path formed in said insulating substrate.

2. The electrode structure of claim 1, wherein said insulating substrate has a wiring layer disposed on said second side of said substrate, said wiring layer connecting said at least one resistive element to a terminal for connection to a power supply.

3. The electrode structure of claim 1, wherein said electrodes of said plurality of electrode elements are electrically connected to said at least one resistive element by wiring.

4. The electrode structure of claim 3, wherein said insulating substrate comprises a substrate extension projecting from a part of said substrate, said wiring comprising a plurality of wires disposed on said substrate extension, said wires being connected to a first connector for wire extension, and said first connector being fixed to said substrate extension.

5. The electrode structure of claim 4, wherein a second connector, being attached to a first end of an electric cable, is electrically connected to said first connector on said first end of said electric cable;
   and wherein a third integration connector, having attached thereto said at least one resistive element, is connected to said second connector on a second end of said electric cable, thereby electrically connecting said at least one resistive element to said electrodes.

6. The electrode structure of claim 1, wherein said electrode of each electrode element has a circular or polygonal shape and an area of less than 1 cm$^2$.

7. The electrode structure of claim 1, wherein said electrode of each of said electrode elements has at least one layer comprising a member selected from the group consisting of carbon, silver, silver chloride, metal foils, binder resins and mixtures thereof.

8. The electrode structure of claim 7, wherein said binder resin comprises a member selected from the group consisting of phenolic resins, polyester resins, epoxy resins, acrylic resins and mixtures thereof.

9. The electrode structure of claim 7, wherein said electrode comprises a carbon layer and a layer comprising silver.

10. The electrode structure of claim 7, wherein said electrode comprises a carbon layer and a layer comprising silver and silver chloride.

11. The electrode structure of claim 7, wherein said electrode has a carbon layer which comprises a composition comprising carbon particles and a binder resin.

12. The electrode structure of claim 1, wherein said resistive element comprises a composition comprising fine carbon particles and a binder resin.

13. The electrode structure of claim 1, wherein said partition is made from a flexible insulating material.

14. The electrode structure of claim 13, wherein said flexible insulating material is selected from the group consisting of silicone resins, styrene thermoplastic elastomers, olefin thermoplastic elastomers, propylene copolymer resins and mixtures thereof.

15. The electrode structure of claim 1, wherein said partition has a shape permitting adhesion to each electrode element and is a formed article having a thickness of not less than 0.1 mm and a height of 1–5 mm.

16. The electrode structure of claim 1, wherein said partition and said insulating substrate form an integrated product.

17. The electrode structure of claim 1, wherein said insulating substrate, said partition or both comprise a material selected from the group consisting of polyimides, polyethylene terephthalates, polypropylenes, polyamides and mixtures thereof.

* * * * *